(12) United States Patent
Nakanishi et al.

(10) Patent No.: US 7,888,079 B2
(45) Date of Patent: Feb. 15, 2011

(54) Nε-ACYL-L-LYSINE-SPECIFIC AMINOACYLASE

(75) Inventors: Kazuhiro Nakanishi, Okayama (JP); Koreyoshi Imamura, Okayama (JP); Hiroyuki Imanaka, Okayama (JP); Mayuko Koreishi, Okayama (JP); Noriki Nio, Kawasaki (JP)

(73) Assignees: Ajinomoto Co., Inc., Tokyo (JP); National University Corporation Okayama University, Okayama-shi (JP)

( * ) Notice: Subject to any disclaimer, the term of this patent is extended or adjusted under 35 U.S.C. 154(b) by 142 days.

(21) Appl. No.: 11/842,457

(22) Filed: Aug. 21, 2007

(65) Prior Publication Data

US 2007/0298469 A1    Dec. 27, 2007

Related U.S. Application Data

(63) Continuation of application No. PCT/JP2006/303047, filed on Feb. 21, 2006.

(30) Foreign Application Priority Data

Feb. 21, 2005  (JP) .............................. 2005-044242

(51) Int. Cl.
  *C12N 9/00*   (2006.01)
  *C12N 11/00*  (2006.01)
  *C12P 1/04*   (2006.01)
(52) U.S. Cl. .................. 435/115; 435/106; 435/170; 435/183; 435/178
(58) Field of Classification Search .................. None
  See application file for complete search history.

(56) References Cited

U.S. PATENT DOCUMENTS

2003/0157670 A1   8/2003   Nakanishi et al.

2004/0106172 A1 *   6/2004   Nakanishi et al. .......... 435/68.1

FOREIGN PATENT DOCUMENTS

| JP | 61-010503 | 1/1986 |
| JP | 2003-210164 | 7/2003 |
| JP | 2004-081107 | 3/2004 |

OTHER PUBLICATIONS

Zhang et al. (2003) Isolation of a Novel Acylase from *Streptomyces mobaraensis* for Syntehsis of Useful Amide Compounds. Kagaku Kogakkai Shuki Taikai Kenkyu Happyo Koen Yoshishu 36: 158.*

Mayuko Koreishi, et al., "Purification and Characterization of a Novel Aminoacylase from *Streptomyces mobaraensis*", Bioscience Biotechnology and Biochemistry, vol. 69, No. 10, XP002502277, Oct. 2005, pp. 1914-1922.

Kurihara, T., et al., Studies on the Compounds Related to Colistin. III. [1)] Synthesis of N-Acyldipeptides and N-Acyltripeptides, Containing Basic Amino Acids, Yakugaku Zasshi, vol. 89, No. 4, 1969, pp. 531-537.

Chibata, I., et al., "∈-Lysine Acylase from *Achromobacter pestifier*," Methods Enzymol., vol. 19, 1970, pp. 756-762.

Asayama, F., et al., "Purification and Chacterization of a Novel Acylase from *Streptomyces mobaraensis*," Nippon Nogei Kagakukan Taikai Koen Yoshishu, 2004, p. 267, 3B04a10, with partial English Translation.

Koreishi, M., et al., "A Novel ∈-Lysine Acylase from *Streptomyces mobaraensis* fro Synthesis of N∈-Acyl-L-lysines," JAOCS, vol. 82, No. 9, 2005, pp. 631-637.

* cited by examiner

*Primary Examiner*—Lisa J Hobbs
(74) *Attorney, Agent, or Firm*—Oblon, Spivak, McClelland, Maier & Neustadt, L.L.P.

(57) ABSTRACT

The present invention provides an aminoacylase having superior abilities in specifically acylating and hydrolyzing ∈-amino group of Lys, and a method of producing Nε-acyl-L-lysine. The present invention provides Nε-acyl-L-lysine-specific aminoacylase containing the amino acid sequence of SERPXTTLLRNGDVH (X unknown) at the N-terminal, and a method of producing Nε-acyl-L-lysine comprising acting the aminoacylase on L-Lys and a carboxylic acid.

10 Claims, 6 Drawing Sheets

LANE 1, 7 ; MARKER
LANE 2 ; CULTURE SUPERNATANT
LANE 3 ; AMMONIUM SULFATE PRECIPITATED FRACTION
LANE 4 ; DEAE SEPHADEX A-50 FRACTION
LANE 5 ; OCTYLSEPHAROSE CL-4B FRACTION
LANE 6 ; PHENYLSEPHAROSE CL-4B FRACTION

SEQUENCE LISTING

```
<160> NUMBER OF SEQ ID NOS: 1

<210> SEQ ID NO 1
<211> LENGTH: 15
<212> TYPE: PRT
<213> ORGANISM: Unknown
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: X = any amino acid

<400> SEQUENCE: 1

Ser Glu Arg Pro Xaa Thr Thr Leu Leu Arg Asn Gly Asp Val His
1               5                   10                  15
```

Nε-ACYL-L-LYSINE-SPECIFIC AMINOACYLASE

CROSS-REFERENCE TO RELATED APPLICATIONS

The present application is a continuation of PCT/JP2006/303047, filed on Feb. 21, 2006, which claims priority to JP 2005-044242, filed on Feb. 21, 2005.

FIELD OF THE INVENTION

The present invention relates to a novel microbial Nε-acyl-L-lysine-specific degrading and synthesizing enzyme, and to a method of producing the same. The present invention also relates to a method of producing Nε-acyl-L-lysine using the enzyme.

BACKGROUND OF THE INVENTION

Because of properties due to its structure and its safeness and harmlessness when released into the environment, Nε-acyl-L-lysine (N-epsilon-acyl-L-lysine) is useful not only as a general cleaning agent in ampholytic detergents, but also in a wide range of industrial fields such as disinfectants, fabric softeners, rust-proofing agents, ore flotation agents, adhesives, clarifying agents, dye fixatives, antistatic agents, emulsifiers, surfactants for cosmetics and the like. In particular, because it dissolves very little in water and common organic solvents and also has water-repellent, antioxidant and lubricating properties, it is being used increasingly in fields such as cosmetics and lubricants as a novel organic powder material (Japanese Patent Application Laid-open (JP-Kokai) No. 61-10503).

Nε-acyl-L-lysine has conventionally been manufactured by dripping an acyl halide into an aqueous alkali solution of an amino acid (Schotten-Baumann method). However, because basic amino acids such as lysine have amino groups in the α-position and ω-position, the principal product of the Schotten-Baumann reaction in this case is a dialkyl basic amino acid, with the ω-acyl basic amino acid being obtained only in small quantities as a by-product. Therefore, for producing ω-acyl basic amino acid, a method is known where a basic amino acid is converted to a copper salt of the acyl amino acid and then acylated with an acyl chloride, after which the copper is removed (Yakugaku Zasshi 89, 531 (1969)). These methods involve complex manufacturing steps and operations, use the heavy metal copper, and require large quantities of hydrogen sulfide gas for the copper removal step.

Consequently, there has been a need for development of enzymes that hydrolyze and synthesize Nε-acyl-L-lysine specifically and efficiently under milder conditions, as well as industrial methods for producing the enzymes.

There have previously been few reports of enzymes capable of specifically hydrolyzing Nε-acyl-L-lysines, and while an enzyme from *Achromobacter pestifer*, one from rat kidneys and one from *Pseudomonas* sp. KT-83 have been reported, Nε-acyl-L-lysine synthesis reactions using these enzymes have not been reported. Moreover, no enzyme has been discovered that specifically and efficiently acylates the ε-amino group of the two amino groups in lysine.

Regarding synthesis of Nε-acyl-L-lysine using conventional enzymes, it has been reported for example that the capsaicin hydrolyzing and synthesizing enzyme described in JP-Kokai No. 2003-210164 also catalyzes an Nε-acyl-L-lysine synthesis reaction.

As described in JP-Kokai No. 2004-81107, it has been reported that Nε-lauroyl-L-lysine is produced with a yield of 95% by the capsaicin hydrolyzing and synthesizing enzyme described in JP-Kokai No. 2003-210164. However, a long reaction time of two days is required, and because this capsaicin hydrolyzing and synthesizing enzyme exhibits high reactivity on the α-amino group as well as the ε-amino group, a mixture of Nα-lauroyl-L-Lys and Nε-lauroyl-L-Lys was eventually produced.

SUMMARY OF THE INVENTION

The present invention provides a novel enzyme with excellent ability to specifically hydrolyze and synthesize Nε-acyl-L-lysine (N-epsilon-acyl-L-lysine) and a method of producing the enzyme as well as a method for producing Nε-acyl-L-lysine (N-epsilon-acyl-L-lysine) using this enzyme.

The inventors discovered that a microorganism belonging to the genus *Streptomyces* produces an enzyme with excellent ability to specifically hydrolyze and synthesize Nε-acyl-L-lysine.

One embodiment of the present invention is an enzyme having the following properties:

1) It acts on Nε-acyl-L-lysine to catalyze a reaction that liberates carboxylic acid and L-lysine, and also catalyzes the reverse reaction thereof;

2) Substrate-specificity: It acts on Nε-acyl-L-lysine having various acyl groups, but has extremely low reactivity on Nε-acyl-D-lysine; it has broad specificity for acyl groups, hydrolyzes Nε-acyl-L-lysine comprising of saturated or unsaturated fatty acid acyls as well as aromatic group carboxylic acid acyls, and also catalyzes the reverse reaction; in the reverse reaction, although it acts on the ε-amino group of L-lysine, it has extremely low reactivity on the ε-amino group of D-lysine, and acts preferentially on the epsilon-amino group of L-lysine;

3) Optimum pH: optimum pH for the hydrolysis reaction is in the range of 8.0 to 9.0 in Tris-HCl buffer at 37° C. when Nε-acyl-L-lysine is used as a substrate;

4) pH stability: It is stable in the range of pH 6.5 to 10.5 when incubated for 1 hour at 37° C.;

5) Optimum temperature: optimum temperature for the hydrolysis reaction is about 55° C. in 50 mM Tris-HCl buffer (pH 8.2) when Nε-acetyl-L-lysine is used as the substrate;

6) Heat stability: It is not inactivated at all by a treatment at 40° C. for 60 minutes in 50 mM Tris-hydrochloric acid buffer (pH 8.2); residual activity thereof after 60 minutes of treatment at 55° C. in the same buffer is about 80% (75 to 85%);

7) Its activity is inhibited by o-phenanthroline;

8) Its activity is increased by cobalt ions;

9) Molecular weight is about 60 K as measured by SDS-polyacrylamide electrophoresis;

10) contains the amino acid sequence of SERPXTTLL-RNGDVH (X unknown) locating at the N-terminal thereof.

One aspect of the present invention is a method for producing the enzyme of the present invention, wherein a microorganism belonging to the genus *Streptomyces* that produces an enzyme with the properties described above (particularly *Streptomyces mobaraensis*) is cultured, and the aforementioned enzyme is isolated and/or collected from the resulting culture.

Another aspect of the present invention is a method of producing Nε-acyl-L-lysine, wherein the enzyme of the present invention is brought into contact with a carboxylic acid and L-lysine or salts thereof to thereby produce Nε-acyl-L-lysine.

Yet another aspect of the present invention is a method of producing Nε-acyl-L-lysine, wherein the enzyme of the present invention is brought into contact with a carboxylic acid having an acyl group with 5 or more carbon atoms or a salt thereof and L-lysine or a salt thereof to thereby produce Nε-acyl-L-lysine.

In a more specific embodiment of the present invention, in the method of producing Nε-acyl-L-lysine described above the carboxylic acid is selected from the group consisting of octanoic acid, decanoic acid, lauric acid, myristic acid, palmitic acid, stearic acid, linoleic acid, linolenic acid, benzoic acid and cinnamic acid.

Another aspect of the present invention is a method of producing Nε-acyl-L-lysine, wherein the contact between the enzyme of the present invention and a carboxylic acid or salt thereof and L-lysine or a salt thereof occurs in a water-soluble solvent.

DESCRIPTION OF THE PREFERRED EMBODIMENTS

Figure 1:
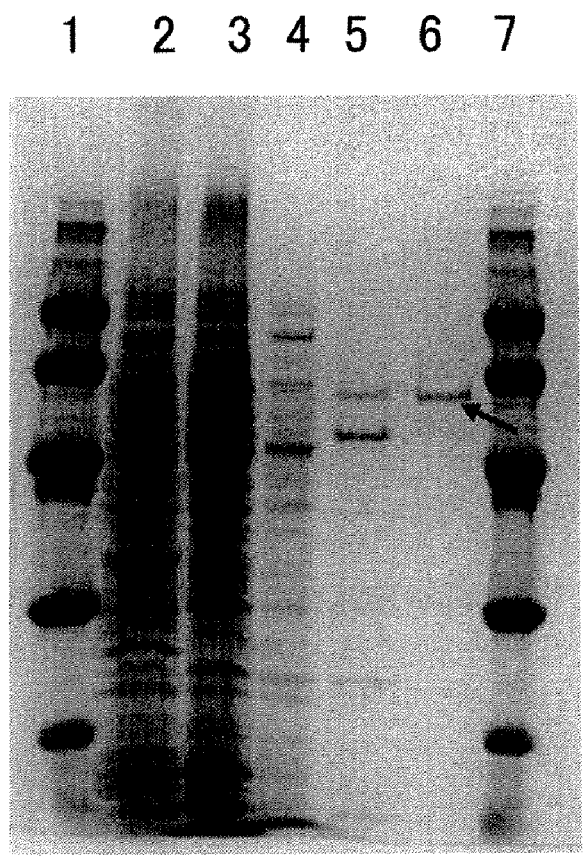
FIG. 1 shows the results of SDS-PAGE of the purified enzyme of the present invention in the presence of the reducing agent 2-mercaptoethanol, with Coomassie brilliant blue staining. Lanes 1, 7: molecular weight markers, Lane 2: culture supernatant, Lane 3: 60% ammonium sulfate precipitated fraction, Lane 4: DEAE-Sephadex A-50 column chromatography eluted fraction, Lane 5: octyl-Sepharose CL-4B column chromatography eluted fraction, Lane 6: phenyl-Sepharose CL-4B column chromatography eluted fraction. Arrows show position of enzyme of invention.

The novel enzyme used in the present invention can be produced by culturing a microorganism. There are no particular limits on the producing organism as long as it has the ability to produce an enzyme having the properties described above, but a microorganism belonging to the genus *Streptomyces* is preferred, and *Streptomyces mobaraensis* is especially preferred. The source of the microorganism belonging to the genus *Streptomyces* is not particularly limited but in the case of *Streptomyces mobaraensis* for example, it is possible to use NBRC (IFO) No. 13819T, which has been deposited at the Institute for Fermentation, Osaka (17-85 Juso-honmachi 2-chome, Yodogawa-ku, Osaka, 532-8686) and transferred to the National Institute of Technology and Evaluation (2-5-8 Kazusakamatari, Kisarazu-shi, Chiba, 292-0818), and ATCC15003, ATCC25365, ATCC27441, ATCC27446 and ATCC29032, which are available from the American Type Culture Collection (ATCC). Variants and/or mutant strains of these strains can also be used to obtain the enzyme of the present invention and/or in the Nε-acyl-L-lysine production method of the present invention.

A microorganism that produces the novel enzyme of the present invention can be cultured according to information known in the field of zymology for the relevant organism. Either a synthetic or natural medium can be used for the medium as long as it contains suitable amounts of a carbon source, nitrogen source, inorganic matter and other nutrients, and either liquid or solid medium can be used for the culture. For particularly carbon sources, one or more can be selected from conventional carbon sources and used according to the needs of the specific microorganism, such as sugars including glucose, fructose, maltose, galactose, starch, hydrolyzed starch, molasses, blackstrap molasses, naturally occurring carbohydrates including wheat, rice, glycerol, alcohols including methanol, ethanol, fatty acids including acetic acid, gluconic acid, pyruvic acid, citric acid, hydrocarbons including normal paraffin, and amino acids including glycine, glutamine, asparagine, and the like. For the nitrogen source, one or more can be selected from organic nitrogen compounds such as animal, plant and microbial hydrolysates including meat extract, peptone, yeast extract, soy hydrolysate, milk casein, casamino acids, various amino acids, corn steep liquor or the like, and inorganic nitrogen compounds including ammonia, ammonium salts such as ammonium nitrate, ammonium sulfate, ammonium chloride, nitrates such as sodium nitrate, and urea and used according to the needs of the specific microorganism. Trace amounts of one or more of phosphoric acid salts, hydrochloric acid salts, sulfuric acid salts, acetic acid salts or the like of magnesium, manganese, calcium, sodium, potassium, copper, zinc or the like may also be selected and used as necessary as inorganic salts. A vegetable oil, surfactant or other antifoaming agent may also be added. A person skilled in the art could select the types and concentrations of the various medium components depending on the microorganism used.

Culture can be conducted in liquid medium containing these medium components by shaking culture, aerobic shaking culture, continuous culture or another conventional method. The culture conditions can be selected appropriately depending on the type of medium and culture method, and may be any conditions under which the microorganism proliferates and produces the enzyme of the present invention. In general, the microorganism is preferably cultured under temperature conditions of 25 to 35° C., with the pH adjusted to 7 at the start of culture. The days of culture may be generally 3 to 7 days when using a 2 liter triangular flask, taking the produced amount of enzyme and the growth conditions of the microorganism and the like into account, but this period is not particularly limited. Under these conditions, the enzyme of the present invention is produced by the microorganism and accumulates in the culture. In particular, medium and conditions suitable for *Streptomyces* and *Streptomyces mobaraensis* in particular are known to those skilled in the art.

Because when *Streptomyces* and *Streptomyces mobaraensis* in particular is cultured, the enzyme is secreted extracellularly from the bacterial cells, a crude enzyme fraction can be easily obtained after completion of culture by removing the cells by a method such as filtration or centrifugation. When another microorganism is used and the enzyme is not released extracellularly, the cells may be crushed by known methods for that microorganism and the cells and cell debris may then be removed by a method such as filtration or centrifugation to obtain the enzyme of the present invention as a crude enzyme fraction. The crude enzyme fraction of the enzyme of the present invention obtained in this way may be hereinafter referred to as a "crude aminoacylase".

The resulting crude aminoacylase can then be purified by one of protein purification methods known to those skilled in the art or a combination thereof, including salt precipitation, differential sedimentation with an organic solvent, ion exchange chromatography, gel filtration chromatography, hydrophobic chromatography, dye chromatography, hydroxyapatite chromatography, affinity chromatography and other chromatography methods or high performance liquid chromatography (HPLC) and electrophoresis. Enzymes having different degrees of purity are obtained at different steps of purification.

The activity of the enzyme of the present invention can be measured based on a method of measuring Nε-acetyl-L-lysine hydrolysis activity. For example, the activity of the enzyme of the present invention may be measured by incubating the enzyme with a defined concentration of Nε-acetyl-L-lysine as a substrate for 30 minutes at 37° C. (50 mM Tris-HCl buffer, pH 8.0), and assaying the released L-lysine. 1 U (unit) of the enzyme of the present invention is defined as the amount of the enzyme required to hydrolyze 1 micromole of Nε-acetyl-L-lysine per hour when incubated for 30 minutes at 37° C. (50 mM Tris-HCl buffer, pH 8.0) with 4 mM Nε-acetyl-L-lysine as the substrate, and the released L-lysine was assayed by the acidic ninhydrin method.

The enzyme of the present invention may be purified for example as follows. After completion of culture of *Streptomyces* bacteria such as *Streptomyces mobaraensis*, the cells are removed by centrifugation and filtration to obtain supernatant containing the novel enzyme. This supernatant is then fractionated by precipitation with ammonium sulfate (2.8 M), and subjected to CM Sephadex C-50, DEAE-Sephadex A-50 ion exchange column chromatography and octyl-Sepharose CL-4B and phenyl-Sepharose CL-4B column chromatography to purify an enzyme of the present invention to such a degree that a single band is present on the gel in polyacrylamide gel electrophoresis.

The enzyme of the present invention acts on Nε-acyl-L-lysine and has extremely low reactivity on Nε-acyl-D-lysine. It has broad specificity for acyl groups, hydrolyzing Nε-acyl-L-lysine comprising saturated or unsaturated fatty acid acyls and carboxylic acid acyls containing aromatic groups, and also catalyzes the reverse reaction. In the reverse reaction it has extremely low reactivity on the ε-amino group of D-lysine, acting preferentially on the ε-amino group of L-lysine.

Another aspect of the present invention is a method of producing Nε-acyl-L-lysine by using the enzyme of the present invention. In one embodiment of this aspect, the enzyme of the present invention is brought into contact with L-lysine or a salt thereof and a carboxylic acid or salt thereof to thereby produce Nε-acyl-L-lysine. The conditions for reacting the enzyme of the present invention in this embodiment can be determined according to the properties of the enzyme of the present invention as described above, particularly the suitable conditions including optimum temperature and stable temperature as well as optimum pH and stable pH. In particular, when the carboxylic acid has a relatively long chain and the contact occurs in a water-soluble solvent, the resulting Nε-acyl-L-lysine precipitates and is easily removed from the reaction system because it is insoluble or poorly soluble in water, and consequently the ε-acyl-L-lysine synthesis reaction progresses much more preferably and efficiently than the reverse Nε-acyl-L-lysine hydrolysis reaction. In such cases, the Nε-acyl-L-lysine can also be collected very easily because it separates rapidly from the water phase. For example, the separated Nε-acyl-L-lysine can be collected directly, or the Nε-acyl-L-lysine can be easily extracted and recovered from the aqueous reaction system with an organic solvent. When Nε-acyl-L-lysine is produced according to the present invention, the relatively long-chain carboxylic acid can be selected for example on the basis of its solubility in the water-soluble solvent used. The carboxylic acid has preferably a long chain, because the solubility of a carboxylic acid in an aqueous solvent reduces as the number of carbon increases. More specifically, the carboxylic acid used in the present invention is preferably a carboxylic acid having an acyl group with 5 or more, preferably 8 or more carbon atoms. However, it is possible to produce Nε-acyl-L-lysine according to the present invention even using a carboxylic acid having an acyl group with 4 or less carbon atoms.

The term "water-soluble solvent" as used herein includes water itself. Even though the reaction is conducted in a water-soluble solvent, an oil layer (organic solvent layer) can be layered on it to form a water-soluble solvent/organic solvent two-phase reaction system.

The "enzyme" used in producing Nε-acyl-L-lysine according to the present invention may be in any form having the enzyme activity of the present invention, including a culture of a microorganism that produces the enzyme of the present invention (in which the microbial cells may be optionally crushed), a culture broth fraction ("crude aminoacylase") obtained by removing the microbes or crushed microbes from the culture (after crushing as necessary) by centrifugation, filtration or the like, a partially purified enzyme which was purified to various degrees from the culture broth (for example, an enzyme partially purified by ammonium sulfate precipitation), or an enzyme purified to a high degree so as to produce a single band on SDS-PAGE.

In one embodiment of the present invention where Nε-acyl-L-lysine is produced by using the enzyme of the present invention, 0.5 to 50 U, preferably 1 to 20 U of the enzyme of the present invention, 50 mM to 2 M, preferably 100 mM to 1.0 M of L-lysine or a salt thereof and 5 mM to 2 M, preferably 10 mM to 150 mM of a carboxylic acid or salt thereof are reacted for 1 to 48 hours or preferably 2 to 24 hours or more preferably 4 to 24 hours at a temperature ranging from 30° C. to 70° C., preferably 45° C. to 70° C. and a pH ranging from pH 6.5 to 10.5, preferably pH 7.0 to 10.0 or more preferably pH 8.0 to 9.0 in a suitable buffer such as Tris-HCl buffer. Nε-acyl-L-lysine can thus be obtained with a yield of about 80% or more under suitable conditions. Alternatively, either L-lysine or carboxylic acid being the substrate may be present in excess in the reaction system, or insufficient substrate may be added as necessary to the reaction system during the course of reaction.

As discussed before, in the Nε-acyl-L-lysine production method of the present invention the enzyme of the present invention catalyzes a reaction between L-lysine and a carboxylic acid or between their salts. The carboxylic acid used in the reaction may be a straight-chain or branched saturated or unsaturated fatty acid or an aromatic carboxylic acid having a saturated or unsaturated side chain, and these carboxylic acids preferably have acyl groups with 5 or more, or preferably 8 or more carbon atoms. More specifically, carboxylic acids that can be used in the method of producing Nε-acyl-L-lysine according to the present invention are preferable to be octanoic acid, decanoic acid, lauric acid, myristic acid, palmitic acid, stearic acid, linoleic acid, linolenic acid, benzoic acid, cinnamic acid and the like, and octanoic acid and lauric acid are particularly preferred.

The present invention is explained in detail below using examples, but these examples should not be construed as limiting the scope of the present invention.

Percentages indicated in the following examples are percentages by weight unless otherwise specified.

EXAMPLES

Example 1

Production and Purification of Aminoacylase of Present Invention

Two (2) liters of medium containing 4.0% soluble starch, 2.0% polypeptone, 4.0% meat extract, 0.2% potassium hydrogen phosphate and 2.0% magnesium sulfate at pH 7 was placed in a 5-liter baffled Sakaguchi (shaking) flask and inoculated with 0.1 ml of *Streptomyces mobaraensis* spore suspension, which was then cultured for 3 to 7 days at 30° C. A total of 2 liters were cultured, and upon completion of culture the cells were removed by centrifugation (10,000×g, 30 min) and the supernatant was collected. The total activity of the resulting enzyme (in supernatant) was 2875 U, and the specific activity was 0.096 U/mg. Quantification of the proteins was conducted by dye binding method.

The activity of the enzyme of the present invention was measured by incubating the enzyme (50 mM Tris-HCl buffer, pH 8.0) for 30 minutes at 37° C. with a defined concentration of Nε-acetyl-L-lysine as the substrate, and assaying the released L-lysine. 1 U (unit) of the enzyme of the present invention is defined as the amount of the enzyme required to hydrolyze 1 micromole of Nε-acetyl-L-lysine per hour at 37° C. for 30 minutes in 50 mM Tris-HCl buffer, pH 8.0 with 4 mM of Nε-acetyl-L-lysine as the substrate, and the released L-lysine was assayed by acidic ninhydrin method.

Ammonium sulfate was added to the resulting culture supernatant to a final concentration of 60%. The resulting precipitate was dissolved in 150 ml of 50 mM NaCl/25 mM Tris-HCl buffer (pH 7.5), and dialyzed with 3 L of 50 mM NaCl/25 mM Tris-HCl buffer (pH 7.5). The resulting enzyme in solution had a total activity of 947 U and a specific activity of 0.43 U/mg.

This active fraction was loaded on a DEAE-Sephadex A-50 column (26 diameter×350 mm) equilibrated with 50 mM NaCl/25 mM Tris-HCl buffer (pH 7.5), and eluted with a 50 to 500 mM NaCl concentration gradient. As a result, an active fraction was eluted at a NaCl concentration of about 250 mM. Total activity was 613 U, and specific activity was 2.1 U/mg.

This active fraction was loaded on an octyl-Sepharose CL-4B column (16 diameter×300 mm) equilibrated with 750 mM NaCl/25 mM Tris-HCl buffer (pH 7.5), with a NaCl concentration gradient of 750 to 0 mM. As a result, an active fraction was eluted at a NaCl concentration of 0 mM. Total activity was 456 U, and specific activity was 304 U/mg.

This active fraction was loaded again on a phenyl-Sepharose CL-4B column (16 diameter×150 mm) equilibrated with 500 mM NaCl/25 mM Tris-HCl buffer (pH 7.5), with a NaCl concentration gradient of 500 to 0 mM. The activity was eluted at a NaCl concentration of 0 mM. Total activity was 169 U, and specific activity was 3370 U/mg.

This active fraction was subjected to polyacrylamide gel electrophoresis, which revealed that it was purified to such a degree that it exhibited a single band with a molecular weight of about 60 k (FIG. 1). The results of purification in each step are shown in Table 1.

The enzyme such purified was subjected to protein sequencing, which showed that it contained the amino acid sequence SERPXTTLLRNGDVH (X unknown) (SEQ ID NO:1) at the N-terminal.

TABLE 1

| | Protein (mg) | Total activity (U) | Yield (%) | Specific activity (U/mg) | Degree of purification (-fold) |
|---|---|---|---|---|---|
| Culture supernatant | 29943 | 2875 | 100 | 0.096 | 1 |
| Ammonium sulfate precipitated fraction | 2183 | 947 | 32.9 | 0.043 | 4.5 |
| DEAE-Sephadex A-50 | 299 | 613 | 21.3 | 2.1 | 22 |
| Octyl-Sepharose CL-4B | 1.5 | 456 | 15.9 | 304 | 3170 |
| Phenyl Sepharose CL-4B | 0.05 | 169 | 5.9 | 3370 | 35100 |

U: units

Example 2

Optimum pH and pH Stability of the Aminoacylase of the Present Invention

The optimum pH and pH stability of the enzyme were measured using the finally purified enzyme obtained by the methods described in Example 1 and Nε-acyl-L-lysine as the substrate.

Figure 2:
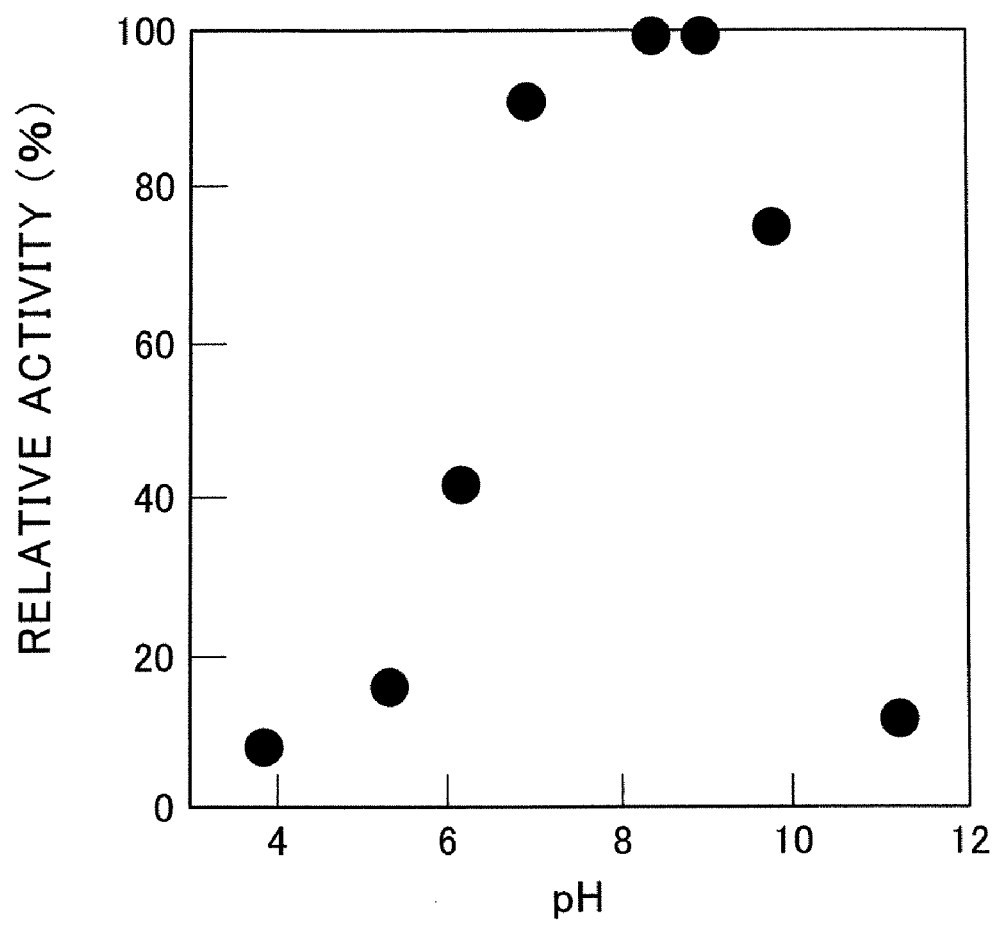
FIG. 2 shows the optimum pH profile of the enzyme of the present invention.
Figure 3:
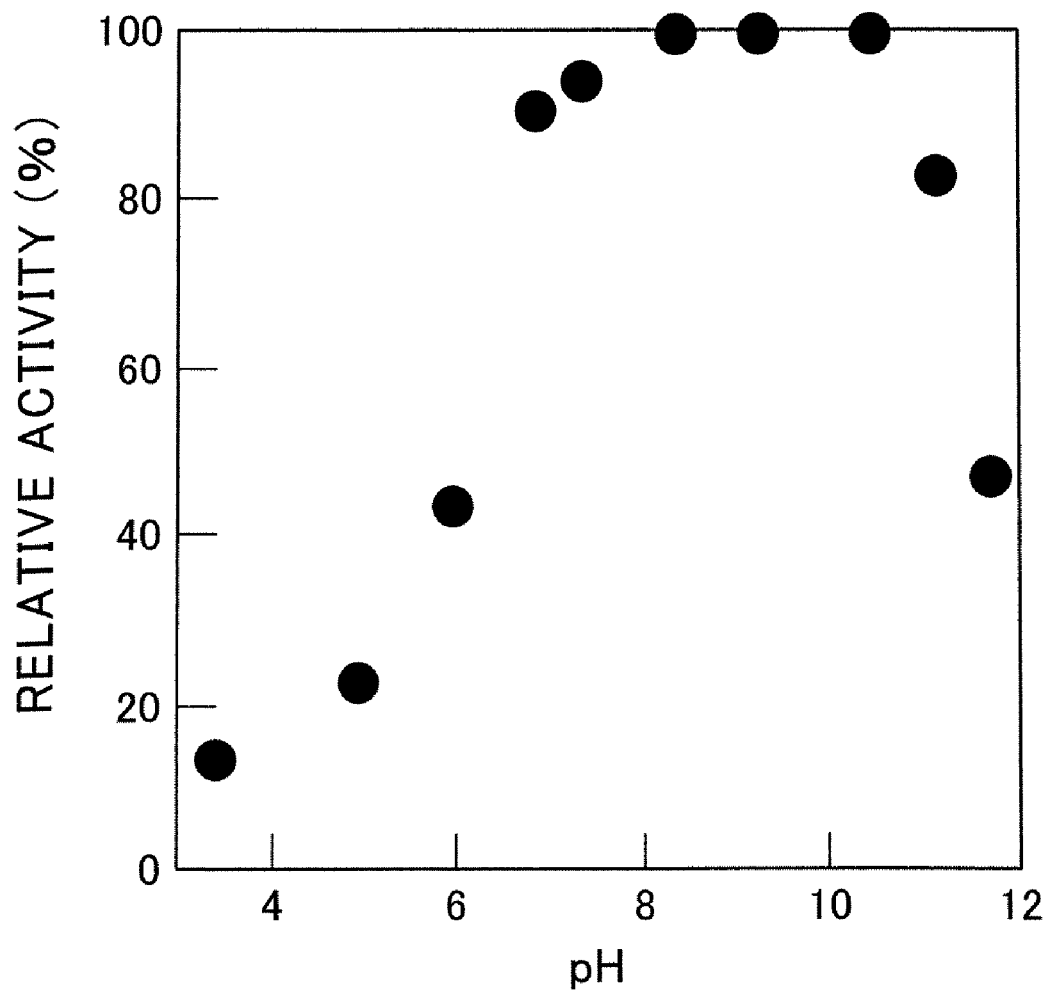
FIG. 3 shows the pH stability profile of the enzyme of the present invention.

Activity was measured at 37° C. at different pH values using different buffers (pH 3.8 to 9.7: Tris-HCl buffer; pH 8.6 to 10.6: CAPS buffer). The results are shown in FIG. 2. In FIG. 2, activity is presented as a relative activity (%) given 100 as activity at the maximum value. As shown by these results, the optimum pH for the enzyme is in the range of 8.0 to 9.0.

pH stability was also investigated. When incubated for 1 hour at 37° C., the enzyme of the present invention was stable at a pH range of 6.5 to 10.5 (FIG. 3).

Figure 4:
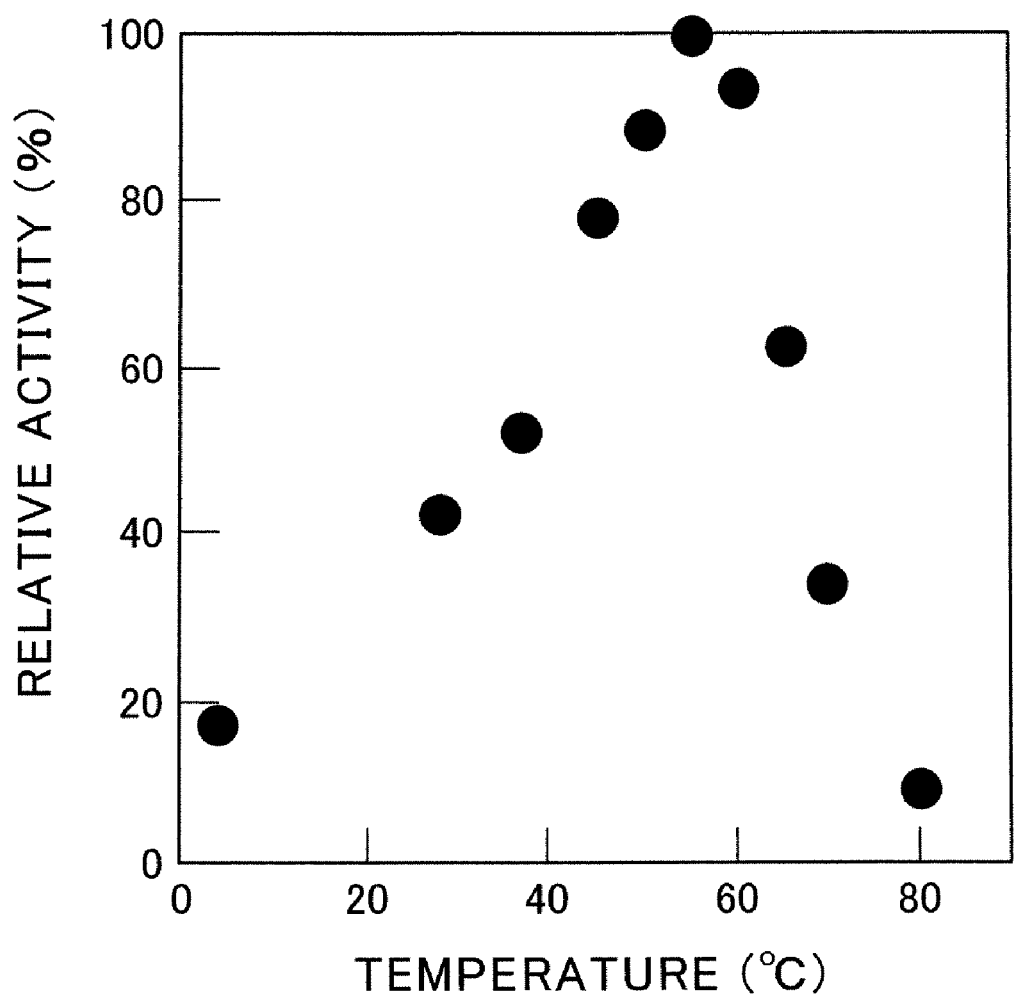
FIG. 4 shows the optimum reaction temperature profile of the enzyme of the present invention.
Figure 5:
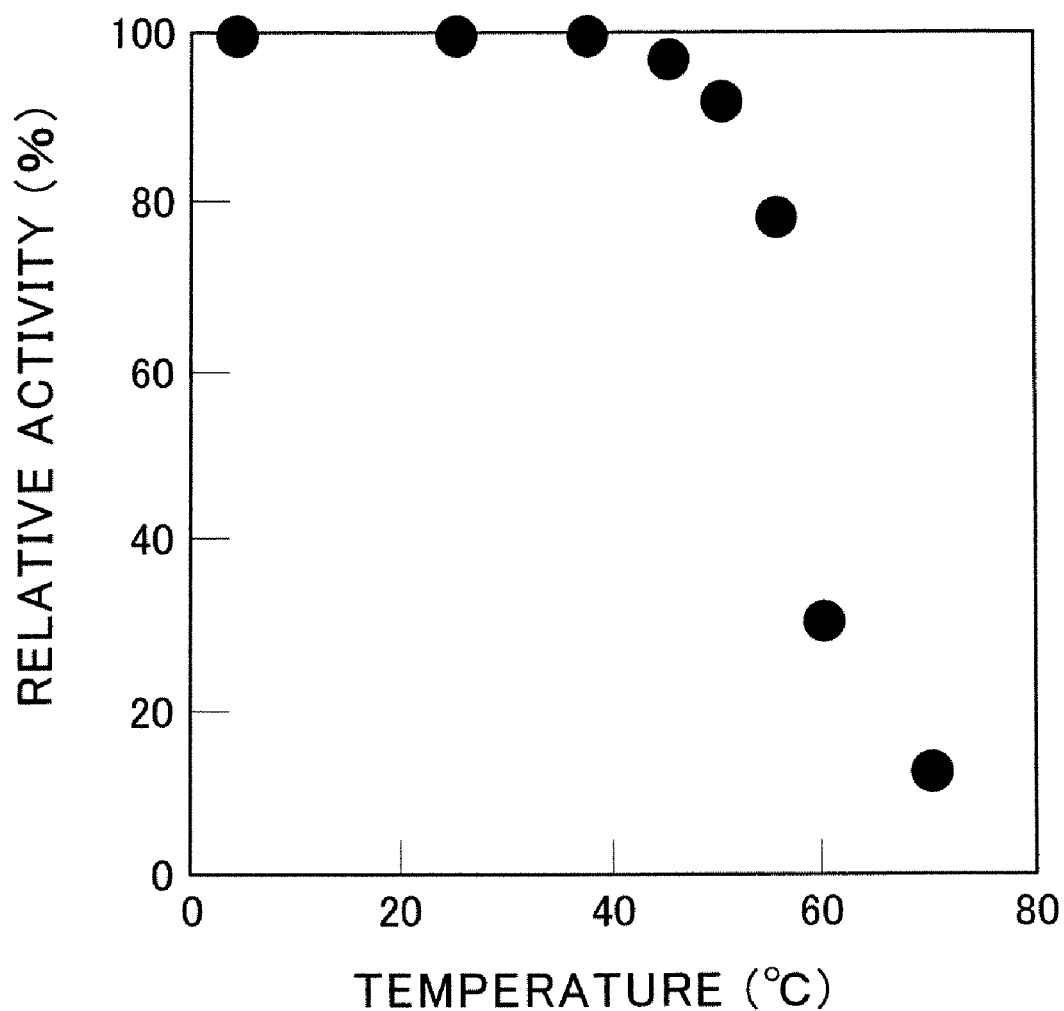
FIG. 5 shows the heat stability profile of the enzyme of the present invention.

The optimum reaction temperature and temperature stability of the enzyme were also measured using the aforementioned purified enzyme, with Nε-acyl-L-lysine as the substrate. The results are shown in FIGS. 4 and 5. In FIGS. 4 and 5, relative activity (%) is shown given 100 as activity at the maximum value.

The activity of enzyme solution (50 mM Tris-HCl buffer, pH 8.2) was measured at the temperatures shown on the horizontal axis to investigate the optimum temperature for the enzyme (FIG. 4). To investigate temperature stability, the enzyme solution (50 mM Tris-HCl buffer, pH 8.2) was also incubated for 60 minutes at each temperature, and residual activity was determined by the aforementioned method used for measuring the activity (FIG. 5).

The optimum temperature was 55° C.

Regarding temperature stability, no decrease in activity was seen up to at least 40° C. when the enzyme was incubated for 60 minutes at each temperature, and residual activity was 80% even at 55° C. (FIG. 5). This enzyme is thus shown to be much more stable than the enzyme from *Achromobacter pestifer*, as can be seen from the fact that the enzyme from *Achromobacter pestifer* exhibited hydrolytic activity on Nε- acyl-L-lysine but is extremely unstable with respect to heat, with activity dropping to 25% after 1 hour of incubation at 37° C.

Example 3

Effect of Various Inhibitors on the Hydrolyzing Activity of the Aminoacylase of the Present Invention The effects of various inhibitors on hydrolysis activity were compared by the measurement methods described above using a purified enzyme obtained as in Example 2. One example of the results is shown in Table 2. In Table 2, the enzyme activity is presented as a relative value (%) given 100 as hydrolysis activity where nothing was added. These results showed that the enzyme of the present invention was a metal enzyme the activity of which was reduced by 0-phenanthroline.

TABLE 2

| | Added concentration (mM) | Relative activity (%) |
|---|---|---|
| Nothing added | — | 100 |
| PCMB | 1 | 86.1 |
| Iodoacetamide | 1 | 83.1 |
| β-mercaptoethanol | 10 | 87.5 |
| DTT | 1 | 64.7 |
| GSH | 1 | 80.0 |
| L-cysteine | 1 | 77.6 |
| EDTA | 1 | 74.6 |
| 0-phenanthroline | 1 | 10.3 |

Example 4

Effects of Metal Ions

The effects of metal ions were investigated using the enzyme that had been dialyzed against 0-phenanthroline solution. The results are shown in Table 3. In Table 3, enzyme activity is presented as a relative activity (%) given 100 as hydrolysis activity with nothing added. Activity was enhanced by metal ions including cobalt, zinc, manganese, calcium, potassium and magnesium, and in particular activity was greatly enhanced by cobalt ions.

TABLE 3

| Metal ions | Final concentration (mM) | Relative activity (%) |
|---|---|---|
| Nothing added | 0 | 100 |
| $CoCl_2$ | 0.1 | 140.8 |
| $ZnSO_4$ | 0.1 | 103.3 |
| $MnSO_4$ | 0.1 | 114.1 |
| $CuSO_4$ | 0.1 | 67.2 |
| $CaCl_2$ | 0.1 | 110.3 |
| KCl | 0.1 | 110.2 |
| $MgSO_4$ | 0.1 | 121.1 |
| $FeSO_4$ | 0.1 | 85.3 |

Example 5

Molecular Weight of Aminoacylase of the Present Invention

The finally purified enzyme obtained by the methods described in Example 1 was subjected to SDS-polyacrylamide electrophoresis. A single band was shown and its molecular weight was about 60 k (FIG. 1). The purified enzyme also exhibited a molecular weight of 57 to 60 k when it was subjected to gel filtration chromatography or non-denaturing PAGE. Thus, the enzyme is thought to exist as a monomer.

Example 6

Reactivity of the Enzyme of the Present Invention on Various N-acetyl-L-Amino Acids The reactivity of the enzyme of the present invention on various N-acetyl-L-amino acids (final concentration 4 mM) was studied to investigate substrate specificity. A list of the results is shown in Table 4. In Tables 4 and 5 below, the amount (micro mole) of substrate (acetyl-L-amino acid) hydrolyzed per 1 mg of enzyme protein in a 1-hour reaction in 50 mM Tris-HCl buffer (pH 8.2) at 37° C. is given as specific activity.

The enzyme showed strong hydrolysis activity on Nε-acetyl-L-lysine. However, it exhibited no activity on Nα-acetyl-L-amino acids except for Nα-acetyl-L-lysine. Thus, this enzyme is shown to be extremely specific for Nε-acetyl-L-lysine.

TABLE 4

Substrate Specificity for N-acetyl-L-amino acids

| Substrate | Specific activity (μmol/mg) (relative activity) |
|---|---|
| Nα-acetyl-L-Arg | ND |
| Nα-acetyl-L-His | ND |
| Nα-acetyl-L-Lys | 70 (2.1%) |
| Nε-acetyl-L-Lys | 3370 (100%) |
| Nα-acetyl-L-Asn | ND |
| Nα-acetyl-L-Gln | ND |
| Nα-acetyl-L-Asp | ND |
| Nα-acetyl-L-Glu | ND |
| Nα-acetyl-L-Ala | ND |
| Nα-acetyl-L-Cys | ND |
| Nα-acetyl-L-Gly | ND |
| Nα-acetyl-L-Leu | ND |
| Nα-acetyl-L-Met | ND |
| Nα-acetyl-L-Phe | ND |
| Nα-acetyl-L-Pro | ND |
| Nα-acetyl-L-Trp | ND |
| Nα-acetyl-L-Tyr | ND |
| Nα-acetyl-L-Val | ND |

ND: below detection limit

Example 7

Substrate Specificity of the Enzyme of the Present Invention

Substrate specificity was investigated based on hydrolysis activity on Nε-acyl-L-lysines with various acyl groups. The enzyme of the present invention was shown to have the highest specific activity on Nε-acetyl-L-lysine, but also exhibited high activity on other Nε-acyl-L-lysines such as those having chloroacetyl or benzoyl groups (Table 5). While an enzyme from A. pestifer that exhibits strong hydrolysis activity on Nε-acyl-L-lysine exhibited very little hydrolysis activity on Nε-lauroyl-L-lysine, the enzyme of the present invention exhibited hydrolysis activity on Nε-lauroyl-L-lysine (Table 5). Moreover, the enzyme of the present invention exhibited no hydrolysis activity on Nα-lauroyl-L-lysine.

TABLE 5

Comparison of activity on acyl groups of Nε-acyl-L-lysine

| | Specific activity μmol/mg) | |
|---|---|---|
| Substrate | *A. pestifer* enzyme | *S. mobaraensis* enzyme |
| Nε-acetyl-L-Lys | 2,700* | 3,370 |
| Nε-chloroacetyl-L-lys | 5,300* | 1,030 |
| Nε-benzoyl-L-Lys | 15,000* | 1,380 |
| Nε-octanoyl-L-Lys | 12,500* | 570 |
| Nε-lauroyl-L-Lys | 0.4 | 28 |
| Nα-lauroyl-L-Lys | — | 0 |

*Chibata et al. (1970), Methods Enzymol. 19, 756-562

Example 8

Production of Nε-Lauroyl-L-Lysine

Ten (10) U of the enzyme of the present invention was added in 100 mM Tris-HCl buffer (pH 7.0) to L-lysine hydrochloride (final concentration of 1 M) and lauric acid (final concentration of 15 mM), and reacted for 3 hours at 45° C. The reaction solution was analyzed by HPLC (YMC-Pack ODS 150×4.6 mm, eluent: 35% acetonitrile solution, pH 2.8, flow rate: 0.8 mL/min). The synthesis yield was about 88% based on fatty acids.

As the reaction progressed, the water insoluble Nε-lauroyl-L-lysine was precipitated. The precipitated Nε-lauroyl-L-lysine was collected by filtration or centrifugation, and washed with water to obtain purified Nε-lauroyl-L-lysine.

Example 9

Comparison of Nε-Lauroyl-L-Lysine Synthesis Capacities of Known Capsaicin Hydrolyzing and Synthesizing Enzymes and the Enzyme of the Present Invention The Nε-lauroyl-L-lysine synthesis capacities of the enzyme of the present invention and the capsaicin hydrolyzing and synthesizing enzyme described in JP-Kokai No. 2004-81107 were compared.

Figure 6A:
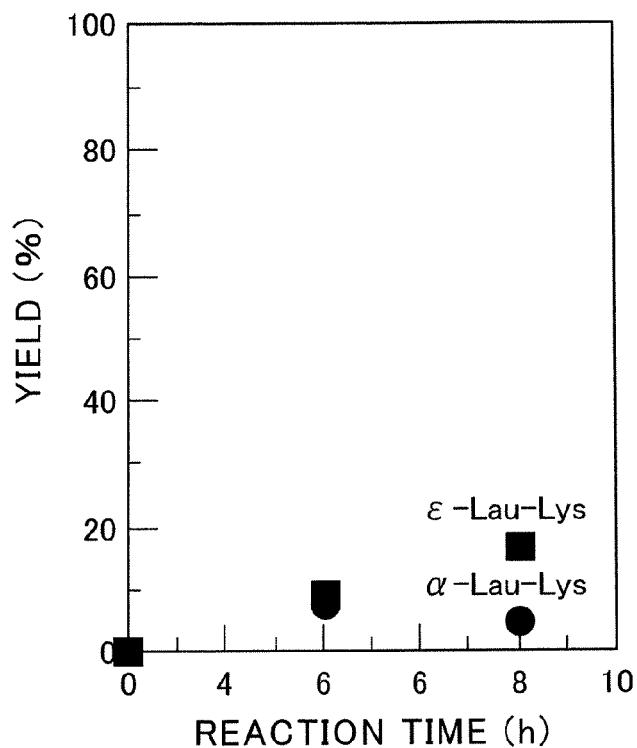
FIG. 6 shows the comparison of the Nε-lauroyl-L-lysine synthesizing ability and specificity of the enzyme of the present invention with those of a known enzyme (JP-Kokai No. 2004-81107). (A) Capsaicin hydrolyzing and synthesizing enzyme, (B) enzyme of present invention. The vertical axis shows yield (%) and the horizontal axis shows the reaction time (hours) in both cases. A black square indicates Nε-lauroyl-L-lysine, and a black circle indicates Nα-lauroyl-L-lysine.
Figure 6B:
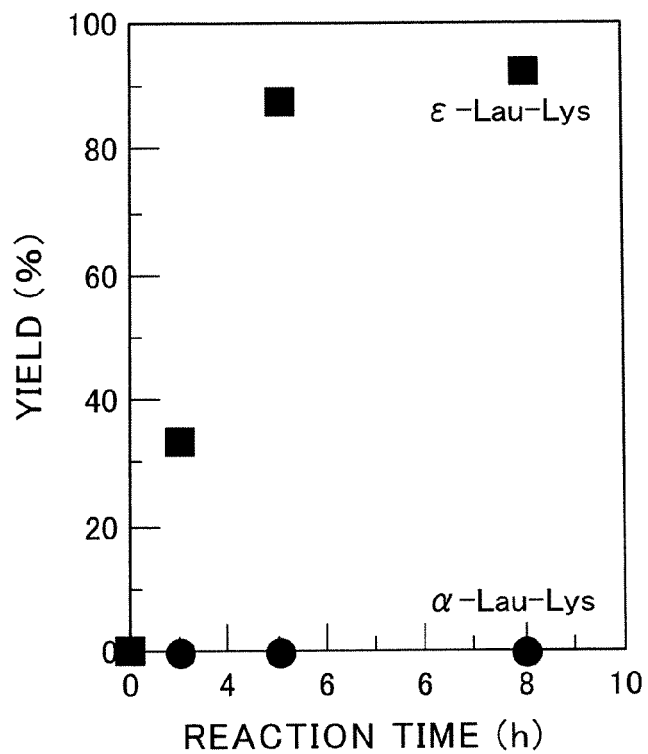

Fifteen (15) mM lauric acid and 200 mM L-lysine hydrochloride were applied at 45° C. on the capsaicin hydrolyzing and synthesizing enzyme (10 U/ml, with 1 U being the amount required to hydrolyze 1 micromole of capsaicin in 1 hour at 37° C., pH 7.7) and the enzyme of the present invention (10 U/ml) in 100 mM Tris-HCl buffer (pH 7.5, 0.5 mM $CoCl_2$), and the amounts of produced Nε-lauroyl-L-lysine were compared (FIG. 6). With a 4-hour reaction, the Nε-lauroyl-L-lysine synthesis yield was about 10% using the capsaicin synthesizing enzyme, and a roughly equal amount of Nε-lauroyl-L-lysine was produced. On the other hand, using the enzyme of the present invention, the Nε-lauroyl-L-lysine synthesis yield was about 90% with a reaction time of 3 hours, and no Nε-lauroyl-L-lysine production was detected.

The present invention provides a novel enzyme (an aminoacylase), a production method therefore and a method for producing an Nε-acyl-L-lysine-specific hydrolyzing and synthesizing enzyme with this enzyme, and thereby allows Nε-acyl-L-lysine to be efficiently hydrolyzed and synthesized using this enzyme.

REFERENCES

1. Japanese Patent Application Laid-open (JP-Kokai) No. 2003-210164
2. JP-Kokai No. 2004-81107

---

---

The invention claimed is:

1. An enzyme, wherein the enzyme has the following properties:
   1) specifically acts on Nε-acyl-L-lysine to catalyze a reaction that releases a carboxylic acid and L-lysine, and also catalyzes the reverse reaction thereof;
   2) acts on epsilon-amino group of L-lysine;
   3) has an optimum pH in the range of 8.0 to 9.0 for hydrolysis reaction in Tris-HCl buffer at 37° C. where Nε-acetyl-L-lysine is used as a substrate;
   4) is stable in the range of pH 6.5 to 10.5 when incubated for 1 hour at 37° C. in Tris-HCl buffer;
   5) has an optimum reaction temperature of about 55° C. for hydrolysis reaction in Tris-HCl buffer (pH 8.2) were Nε-acetyl-L-lysine is used as a substrate;
   6) is not inactivated by a treatment at 40° C. for 60 minutes in Tris-HCl buffer (pH 8.2), and retains 75 to 85% residual activity after 60 minutes of treatment at 55° C.;
   7) is inhibited by o-phenanthroline;
   8) an activity thereof is increased by cobalt ions;
   9) a molecular weight thereof is about 60 k as measured by SDS-polyacrylamide electrophoresis;

10) amino acid sequence of SEQ ID NO: 1 locates at the N-terminal thereof;
11) activity on Nα-acetyl-L-Lys is 2.1% or less of the activity on Nε-acetyl-L-Lys; and
12) is inhibited by L-Cys.

2. The enzyme according to claim 1, which is obtainable from a microorganism belonging to genus *Streptomyces*.

3. The enzyme according to claim 2, wherein the microorganism belonging to genus *Streptomyces* is *Streptomyces mobaraensis*.

4. A method for producing the enzyme according to claim 1, comprising culturing a microorganism belonging to genus *Streptomyces*.

5. The method according to claim 4, wherein the microorganism belonging to genus *Streptomyces* is *Streptomyces mobaraensis*.

6. A method for producing Nε-acyl-L-lysine, comprising bringing the enzyme according to claim 1 into contact with a carboxylic acid or salt thereof and L-lysine or a salt thereof, and thereby producing Nε-acyl-L-lysine.

7. The method according to claim 6, wherein the carboxylic acid is a carboxylic acid having an acyl group with 5 or more carbon atoms.

8. The method according to claim 6, wherein the carboxylic acid is selected from the group consisting of octanoic acid, decanoic acid, lauric acid, myristic acid, palmitic acid, stearic acid, linoleic acid, linolenic acid, benzoic acid and cinnamic acid.

9. The method according to claim 6, wherein the carboxylic acid is lauric acid and the Nε-acyl-L-lysine is Nε-lauroyl-L-lysine.

10. The method according to claim 6, wherein the contact occurs in a water-soluble solvent.

\* \* \* \* \*